United States Patent
Biber (10) Patent No.: US 8,948,844 B2
(45) Date of Patent: Feb. 3, 2015

(54) BREAST COIL FOR MAGNETIC RESONANCE RECORDINGS OF THE BREAST

(71) Applicant: Stephan Biber, Erlangen/Frauenaurach (DE)

(72) Inventor: Stephan Biber, Erlangen/Frauenaurach (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/723,538

(22) Filed: Dec. 21, 2012

(65) Prior Publication Data

US 2013/0165768 A1    Jun. 27, 2013

(30) Foreign Application Priority Data

Dec. 21, 2011  (DE) .......................... 10 2011 089 448

(51) Int. Cl.
| | |
|---|---|
| A61B 5/05 | (2006.01) |
| A61B 5/055 | (2006.01) |
| G01R 33/3415 | (2006.01) |
| G01R 33/565 | (2006.01) |
| G01R 33/36 | (2006.01) |
| A61B 5/00 | (2006.01) |

(52) U.S. Cl.
CPC ............ A61B 5/055 (2013.01); G01R 33/3415 (2013.01); G01R 33/5659 (2013.01); G01R 33/3642 (2013.01); A61B 5/708 (2013.01); A61B 5/4312 (2013.01); A61B 5/0555 (2013.01)
USPC ............................. 600/422; 600/410; 324/322

(58) Field of Classification Search
USPC ............................. 600/407–429; 324/309–322
See application file for complete search history.

(56) References Cited

U.S. PATENT DOCUMENTS

| | | | | |
|---|---|---|---|---|
| 7,550,973 | B2 * | 6/2009 | Greim et al. | 324/309 |
| 7,772,846 | B2 * | 8/2010 | Roland | 324/309 |
| 7,800,368 | B2 * | 9/2010 | Vaughan et al. | 324/318 |
| 2003/0094947 | A1 * | 5/2003 | Akgun | 324/309 |
| 2007/0285094 | A1 * | 12/2007 | Reeder et al. | 324/313 |
| 2008/0129298 | A1 * | 6/2008 | Vaughan et al. | 324/322 |
| 2010/0099978 | A1 * | 4/2010 | Geppert et al. | 600/422 |
| 2012/0274326 | A1 * | 11/2012 | Lee et al. | 324/318 |

FOREIGN PATENT DOCUMENTS

| | | |
|---|---|---|
| DE | 10 2007 013 996 A1 | 9/2008 |
| DE | 10 2008 048 291 A1 | 4/2010 |

OTHER PUBLICATIONS

German Office Action dated Aug. 3, 2012 for corresponding German Patent Application No. DE 10 2011 089 448.9 with English translation.

* cited by examiner

*Primary Examiner* — Sanjay Cattungal
(74) *Attorney, Agent, or Firm* — Lempia Summerfield Katz LLC (57) ABSTRACT

A breast coil for a magnetic resonance tomography device for the production of magnetic resonance recordings of female breasts includes a coil housing having a breast recess to accommodate a breast and a number of coil elements. At least one of the coil elements forms an HF correction coil element and has a circuit arrangement to switch over the HF correction coil element between an HF correction mode of operation and another mode of operation. The HF correction coil element is constructed such that in the HF correction mode of operation, the HF correction coil element resonates passively with a $B_1$ field emitted by a transmission antenna arrangement of the magnetic resonance tomography device, and influences a local $B_1$ field distribution during a magnetic resonance recording.

20 Claims, 7 Drawing Sheets

BREAST COIL FOR MAGNETIC RESONANCE RECORDINGS OF THE BREAST

This application claims the benefit of DE 10 2011 089 448.9, filed on Dec. 21, 2011, which is hereby incorporated by reference.

BACKGROUND

The present embodiments relate to a breast coil for a magnetic resonance tomography device.

With the increasing spread of magnetic resonance tomography, more and more breast investigations are being carried out with the help of this imaging method. One advantage lies in the fact that, unlike the customary mammographic methods, magnetic resonance tomography does not subject the breast to X-ray doses. In a magnetic resonance tomography device, the body or body region that is to be investigated is customarily exposed to a defined magnetic field (e.g., the $B_0$ field) with the help of a basic magnetic field system. In addition, a magnetic field gradient is applied with the help of a gradient system. Via a high-frequency transmission signal and using suitable antennas, high-frequency magnetic resonance excitation signals (HF signals) are emitted with a defined field strength. The emission of the high-frequency signals for the purpose of nuclear spin magnetization may be effected using a "whole-body coil" or "body coil" (e.g., a birdcage antenna) permanently built into the magnetic resonance tomograph. The whole-body coil surrounds the measurement space (e.g., the "patient tunnel"), in which the female patient is positioned during the investigation. The magnetic flux density of this excitation field may be referred to as $B_1$ and, accordingly, the pulsed high-frequency field is also referred to as the $B_1$ field. Using these HF pulses, the nuclear spin of certain atoms, which are resonantly excited by the $B_1$ field, is tilted by a defined flip angle relative to the magnetic field lines of the $B_0$ field. Relaxation of the nuclear spin is accompanied by the re-emission of high frequency signals (e.g., magnetic resonance signals). The magnetic resonance signals may be received using the whole body coil. For this purpose, local coils that have a higher signal/noise ratio may be used. These are antenna systems affixed in the immediate neighborhood of the patient. The magnetic resonance signals induce a voltage in the individual antennas of the local coils. The induced voltage is then amplified using a low-noise preamplifier (LNA, preamp) and is forwarded to the receiving electronics. Over the course of time, special local coils have been made available for the most varied of application situations (e.g., head coils for investigations in the region of the head or the breast coils mentioned for investigations on female breasts). Such a breast coil may have a coil housing (e.g., with two breast recesses that have a roughly circular cross-section and are arranged beside each other, in which the breasts are accommodated). Arranged in the housing and around the breasts there may, for example, be several coil elements in the form of conducting loops with appropriate electronic components.

From the magnetic resonance signals that are acquired or the "raw data", the desired magnetic resonance image data (MR image data) may be reconstructed. Location encoding is effected by the switching of appropriate magnetic field gradients in the various spatial directions at precisely defined times (e.g., during the emission of the HF signals and/or on receipt of the magnetic resonance signals). Each image point in the magnetic resonance image is, for example, assigned to a small spatial volume (e.g., a so-called voxel), and each brightness or intensity value of the image points is linked to the signal amplitude of the magnetic resonance signal received from this voxel. The relationship between an HF pulse resonantly radiated-in with a field strength $B_1$ and the flip angle $\alpha$ produced by this is given by the equation $$\alpha = \int_{t=0}^{\tau} \gamma \cdot B_1(t) \cdot dt \tag{1}$$

where $\gamma$ is the gyromagnetic ratio that, for most nuclear spin investigations, may be regarded as a fixed material constant. $\tau$ is the duration of application of the high frequency pulse. The flip angle produced by an emitted HF pulse, and hence the strength of the magnetic resonance signal, consequently depends on the duration of the HF pulse and the strength of the irradiated $B_1$ field. Spatial fluctuations in the field strength of the excitation $B_1$ field thus lead to unwanted variations in the magnetic resonance signal received, which may falsify the resulting measurement.

An unfavorable feature is that it is at high magnetic field strengths (e.g., inevitably present in a magnetic resonance tomograph due to the basic magnetic field $B_0$ required) that inhomogeneous penetration characteristics are exhibited in conductive and dielectric media such as, for example, tissues. A result of this is that the $B_1$ field within the measured volume may vary greatly. In the case of the high Larmor frequencies, used for ultra-high field magnetic resonance investigations, the conductivity of the tissue is high. This leads to especially large inhomogeneities, so that in the case of magnetic resonance measurements with a basic magnetic field of three Tesla or more, special measures are to be taken in order that an adequately homogeneous distribution of the HF field transmitted by the high-frequency antenna is achieved through the entire volume. In the case of breast imaging, eddy currents arise in the patient's body (e.g., in the region of the thorax or abdomen) or in the individual breasts with the high basic field strengths due to the $B_1$ field. These lead to an asymmetric distortion of the $B_1$ field (e.g., of the transmitted excitation field) and often to an overshadowing of deeper-lying tissues. In the breasts, this produces both a $B_1$ field pattern with a left/right oriented asymmetry and also a substantial asymmetry in the contrast for the left breast compared to the right breast. This unwanted inhomogeneity has a detrimental effect on the diagnostic relevance or predictive capacity of the magnetic resonance images produced.

In order to reduce the distortion of the $B_1$ field by the patient's body, the body coil is driven such that the body coil transmits with a permanently-set elliptical polarization in order to counteract the asymmetry of the patient's body caused by the greater elongation in the right/left direction than in the anterior/posterior direction. Alternatively, for the purpose of adapting the $B_1$ field, a system of transmission antennas, in which two or more are used as two independent channels, is used so that the amplitude relationship and phase relationship between these channels may be individually adjusted. However, such transmission systems are relatively expensive. In addition, this does not solve the problems for magnetic resonance tomography devices that already exist.

SUMMARY AND DESCRIPTION

The present embodiments may obviate one or more of the drawbacks or limitations in the related art. For example, an improved breast coil and an improved method for the production of magnetic resonance recordings of the female breast are provided.

A breast coil includes a coil housing with a breast recess to accommodate a breast, and a number of coil elements. The breast coil may be a breast coil, with which only magnetic resonance recordings of a single breast may be produced. In this case, one breast recess is sufficient. However, in one embodiment, a breast coil with a coil housing having two breast recesses arranged beside each other that, for example, are roughly circular shaped in cross-section is provided. Both breasts may be laid in the breast recesses at the same time, and a complete recording of the entire breast region may be produced.

The breast coil has at least one coil element that forms an HF correction coil element and for this purpose has a circuit arrangement for switching over the coil element between an HF correction mode of operation and another mode of operation. The HF correction coil element is constructed such that, in the HF correction mode of operation, the HF correction coil element resonates passively with a $B_1$ field emitted by a transmission antenna arrangement of the magnetic resonance tomography device. During a magnetic resonance recording, the HF correction coil element influences the local $B_1$ distribution in a defined way, for example, so as to homogenize the $B_1$ field as far as possible.

If such an HF correction coil element is switched into the HF correction mode of operation, then the coil element is switched by the circuit arrangement such that the coil element is inductively excited by the transmitted $B_1$ field as soon as the transmitted $B_1$ field is emitted in the transmission mode of the magnetic resonance tomography device. As a consequence of this, the HF correction coil element transmits a correction field that destructively or constructively overlays the $B_1$ field the HF correction coil element receives. The strength, with which the HF correction coil element resonates, and whether a destructive or constructive overlaying of the field arises depend on how the self-resonant frequency of the HF correction coil element is set (e.g., whether the self-resonant frequency lies below or above the magnetic resonance frequency used; the Larmor frequency of, for example, about 125 MHz in the case of a 3 Tesla basic magnetic field).

The other mode of operation, into which the coil element may be switched, may be a deactivated state, for example, in which the self-resonant frequency of the coil element is tuned so far away from the magnetic resonance frequency that is being used that the coil is virtually "invisible," and hence is deactivated. This mode of operation is logical if the HF correction coil element is not to be used for receiving, so that the HF correction coil element produces no interference in the receiving situation. However, if the coil element is also to be used for receiving, the other mode of operation may also be a receiving state, in which the self-resonant frequency is tuned as well as possible to the magnetic resonance frequency that is being used. This is explained further below.

Apart from the usual conventional components (e.g., a transmitting antenna arrangement), a magnetic resonance tomography device for producing magnetic resonance recordings of a female breast also has a breast coil that may be used as a local coil within this magnetic resonance tomography device.

In the case of a method for producing magnetic resonance recordings of female breasts for the acquisition of magnetic resonance signals, a $B_1$ field is emitted in the normal way by the transmitting antenna arrangement, and magnetic resonance signals that are excited in the breast as a result of the $B_1$ field are received by a coil element (e.g., several coil elements) in the breast coil. In one embodiment, when this is being done, a coil element in the breast coil is switched as an HF correction element into an HF correction mode of operation when the $B_1$ field is being emitted (e.g., in the transmission mode of the magnetic resonance tomography device, so that the coil element concerned resonates passively with the $B_1$ field, and the desired advantageous effect on the $B_1$ field is produced).

The present embodiments provide an improvement (e.g., a homogenization) of the $B_1$ field distribution so that overall better magnetic resonance images may be produced. The breast coil and the method may also be used on existing magnetic resonance tomography devices without the existing magnetic resonance tomography devices needing first to be converted.

The description in one category may be developed in accordance with the description in another category.

In one embodiment, one or more of the HF correction coil elements may be switched into a receiving mode of operation in order to receive a magnetic resonance signal and to pass the magnetic resonance signal on to a processing unit (e.g., the usual receiving channels of the magnetic resonance tomography device). As an example, the HF correction coil element may for this purpose be connected such that the HF correction coil element has a self-resonant frequency that corresponds to the magnetic resonance frequency used. The circuit arrangement may also be connected into a preamplifier, through which the magnetic resonance signal that is received may be amplified and may be preprocessed in a number of ways. With the use of this type of coil element, the number of coil elements that are to be built into the breast coil is less overall, because dual use of these coil elements is possible.

In one alternative embodiment, the breast coil has a coil element arrangement that incorporates a number of receiving coil elements, each of which is constructed to receive a magnetic resonance signal and to pass the magnetic resonance signal on to a processing unit, together with a number of separate HF correction coil elements that may not be switched over to a receiving mode of operation (e.g., do not serve as receiving coil elements). If the receiving coil elements are, in accordance with another variant, pure receiving coil elements and may not be used as HF correction coil elements, there is a complete functional separation of the transmission coil elements and the correction coil elements. In this case, the individual coil elements may be of somewhat simpler construction. In one mode of operation, the HF correction coil elements may be capable of being detuned so far relative to the magnetic resonance frequency used that the HF correction coil elements are broadly invisible or deactivated, as applicable.

For this embodiment, the pure receiving coil elements may, without difficulty, be configured such that the receiving coil elements may be used as transmission coil elements at the same time in order to emit a $B_1$ field from the breast coil.

There are various possibilities for the configuration of the circuit arrangement for the HF correction coil elements.

The circuit arrangement may be configured such that the HF correction coil element may be switched between several discrete HF correction modes of operation. For example, the circuit arrangement may have several switching stages, for example, in order to connect several capacitances individually in parallel in order to gradually reach particular self-resonant frequencies. How strongly the coil resonates and whether the coil overlays the $B_1$ field destructively or constructively may be controlled adaptively in defined stages.

With another variant, the circuit arrangement is configured such that the HF correction coil element may be adjusted steplessly between different HF correction operating modes. How strongly the coil resonates (e.g., destructively or constructively), in that the self-resonant frequency may be adjusted arbitrarily within a certain bandwidth, may be controlled relatively finely. For this purpose, the circuit arrangement may, for example, have a tunable capacitance (e.g., a capacitive diode such as a varicap diode) that may be driven electronically. In this case, care is to be taken that the voltage endurance is adequate.

In one embodiment, various HF correction coil elements may be used in a breast coil, with circuit arrangements different from the circuit arrangements mentioned above.

The usual magnetic resonance tomography devices emit a circularly polarized $B_1$ field into the measurement space, where the polarization vector rotates about the field direction of the basic magnetic field ($B_0$ field) (e.g., about the longitudinal direction of the measurement space that may correspond to the longitudinal direction of the patient's body). This longitudinal direction may be referred to as the z direction.

In order to effect adequate coupling with such a $B_1$ field, the breast coil in one embodiment has at least one HF correction coil element that is configured and arranged such that the at least one HF correction coil element mainly (e.g., predominantly) detects a $B_1$ field that is polarized in a direction that runs essentially perpendicular to an imaginary plane of the openings in the breast recesses that lies in a chest support area, on which the upper body of the patient is placed or lands. This direction is referred to below as the y direction. The y direction runs roughly in the posterior/anterior direction through the upper body. Here, "essentially perpendicular" may be that there is only a small angle (e.g., a maximum of 20°).

This may be achieved, for example, in that the HF correction coil element has a conducting loop in or on the coil housing that runs essentially (e.g., except for small deviations) circularly around an opening in a breast recess. The effective antenna area formed by this conducting loop lies parallel to the aforementioned chest support area, from which the breast recesses extend out into the breast coil.

The breast coil may also have at least one HF correction coil element that is configured and arranged such that the at least one HF correction coil element mainly (e.g., predominantly) detects a $B_1$ field that is polarized in a direction that runs essentially (e.g., with an angular deviation of at most 20°) parallel to the plane of the opening in a breast recess and perpendicular to a longitudinal axis of the patient's body. This direction is referred to below as the x direction. In the case of the normal arrangement of conventional breast coils with two recesses, affixed in the patient tunnel, this x direction runs parallel to an imaginary straight direct connecting line between the two breast recesses (e.g., in the left/right direction through the upper body).

Such an arrangement may be realized, for example, in that the HF correction coil element has a conducting loop in or on the coil housing. The conducting loop runs beside the side of a breast recess such that a normal to the plane of one of the antenna areas enclosed by the conducting loop lies in a direction that runs essentially parallel to the plane of the opening in a breast recess and at an angle to the longitudinal axis of the patient's body (e.g., the x direction). In other words, the antenna plane thus lies transverse to the connecting axis between the two breast recesses of a breast coil.

In one embodiment, the breast coil has a combination of the various HF correction coil elements, so that some HF correction coil elements detect principally the $B_1$ field that is polarized in the x direction, and the other HF correction coil elements detect principally the $B_1$ field that is polarized in the y direction. Correspondingly, the $B_1$ field may be manipulated in the x and y directions, and consequently also a field that is circularly or elliptically polarized.

In order to achieve the desired homogenization of the $B_1$ field or some other desired field distribution, the circuit arrangements of the individual HF correction coil elements may be driven in an appropriate way by correction signals (e.g., via control signal lines). In other words, the various circuit states of the HF correction coil elements (e.g., switch on/switch off/resonating constructively or destructively with varying strengths) are controlled, for example, from within a central controller of the device.

For this purpose, before an actual useful magnetic resonance measurement or, if appropriate, in pauses between individual measurement sequences, $B_1$ field distribution data that represents a $B_1$ field distribution and/or the deviation of a current $B_1$ field distribution from a target $B_1$ field distribution is detected (e.g., in an adjustment procedure such as a prescan measurement), and on the basis of this suitable correction, control signals are determined. These correction control signals may be used in driving the HF correction coil element during the useful magnetic resonance measurements. For this purpose, the magnetic resonance tomography devices use a correction signal generation device that is configured to generate, on the basis of the $B_1$ field distribution data, a correction control signal for an HF correction coil element. The magnetic resonance tomography devices also use an HF correction control signal interface for outputting the correction control signal to an HF correction coil element, or to the circuit arrangement of the HF correction coil element, as appropriate.

The data used for this purpose, about the characteristics of the coil (e.g., the field distribution that the resonating HF correction coil elements produce depending on the circuit state and for which excitation fields) may be communicated to the system or to the correction signal generation device in a hardware description file ("coil file") that specifies the effect of the resonating HF correction coil element on the $B_1$ field as a function of the transmission field and the circuit state of the $B_1$ correction coils.

Adjustment with the help of the measured $B_1$ field distribution may be effected by repeated experimentation, in that the correction coil elements are retuned after each $B_1$ field measurement, and the $B_1$ field distribution achieved is checked. In doing so, a certain number of HF correction modes of operation may be automatically tried out one after another. For example, in the case of a circuit arrangement with discrete circuit states, all the discrete circuit states may be tried in order to find the ideal circuit state. Alternatively, an intelligent algorithm that may lead to rapid convergence (e.g., an iterative method) may also be used. Common $B_1$ shimming methods that, for example, are otherwise used for the adjustment of several independent transmission channels may be used.

Examples of the possible $B_1$ field distribution data are the usual $B_1$ maps that may be determined in an MR adjustment experiment or even from other previous useful measurements. In this case, the magnetic resonance tomography device or the correction signal generation device, as applicable, use a $B_1$ map input interface.

With one alternative method, the signals induced in the correction coil elements by the transmission field may serve as a measure of the $B_1$ distribution. For this purpose, the HF correction coil element may have an interface for the measurement of an electrical magnitude present at the HF correction coil element during an HF correction mode of operation. Examples of the electrical magnitude may be magnitudes induced by the current $B_1$ field such as voltage amplitudes and/or phases. In the case when an HF correction coil element serves at the same time as a transmission coil element, the connection to the preamplifier, with which the induced magnetic resonance signal is tapped off in the receiving situation, may also serve as the interface for these electrical magnitudes. The use of such simple electrical magnitudes, which are induced in the HF correction coil elements during the emission of the $B_1$ field, has the advantage that the measurements are very rapid, because the measurements do not use a determination of a spatial distribution of the $B_1$ field.

In one embodiment, a combination of the two methods is carried out (e.g., in an initial adjustment measurement), and compensation is effected using the $B_1$ maps in order to achieve as closely as possible the target $B_1$ field distribution. The electrical magnitudes induced in the HF correction coil elements by the $B_1$ field are also measured and are used as reference values for later re-adjustments. At a later stage, during the useful magnetic resonance measurement, simple online checking and retro-correction may be effected using the induced electrical magnitudes.

In a further embodiment, the detuning of the HF correction coil elements and the constructive or destructive contribution to the $B_1$ field from the transmission antenna arrangement of the magnetic resonance tomography device may also be varied by rapid switching over or driving during the measurement. Dynamic $B_1$ shimming by, for example, a layer-dependent selection of the $B_1$ characteristics of the breast coil may thus be provided. With this, the oscillatory characteristics of the HF correction coil elements may be changed from one layer to another, for example, during layerwise recording. In one embodiment, changes may be made as a function of another magnetic resonance sequence parameter.

Extremely rapid switchover and control of the resonance characteristics of the HF correction coil elements is also possible during a transmission pulse. Such a transmission pulse may last between 1 and 20 ms. The relevant HF correction coil element may be tuned within this time interval by adjusting the self-resonant frequency to the desired magnitude.

BRIEF DESCRIPTION OF THE DRAWINGS

Components that are the same in the various figures have been given the same reference characters.

DETAILED DESCRIPTION OF THE DRAWINGS

Figure 1:
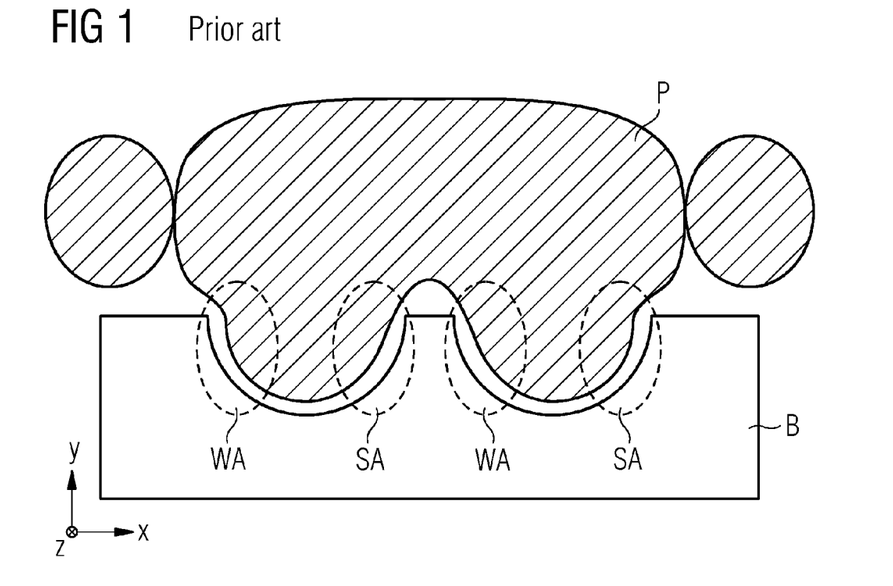
FIG. 1 shows a cross-section through a female patient with a conventional breast coil to illustrate the $B_1$ field distribution problems.

FIG. 1 shows the problems that arise with a breast coil B conforming to the prior art (e.g., the inhomogeneous spatial distribution of the $B_1$ field). FIG. 1 shows a cross-section through a female patient P who is lying on a breast coil B, shown in a rough schematic form. The axis of the body of the patient P is, for example, correlated with the lengthwise axis in the z direction within the patient tunnel (see FIG. 9). With the notation used here and below, the y direction runs in the anterior/posterior direction and the x direction from right to left relative to the patient's body (e.g., from left to right in the illustration).

The $B_1$ field produces eddy currents in the thorax and in the patient's individual breasts, which may also lead to overshadowing of the $B_1$ amplitude in the thorax and in the breasts. Thus, this may also lead to an asymmetric $B_1$ field distribution in the region of the breasts. This may lead to a left-right asymmetry arising in each individual breast, whereby in each of the breasts, a region WA occurs on one side (e.g., the left) with a lower $B_1$ amplitude. On the right-hand side, there is a region SA with a higher $B_1$ amplitude. In addition, there may also be a global asymmetry across the entire breast region. As explained in the introduction, these local variations in the $B_1$ field distribution lead to corresponding variations and may also lead to artifacts in the magnetic resonance image data produced. This example is shown in FIG. 1. In principle, however, quite different asymmetric distributions may develop depending on the patient's anatomy and the geometry of the excitation field.

Figure 2:
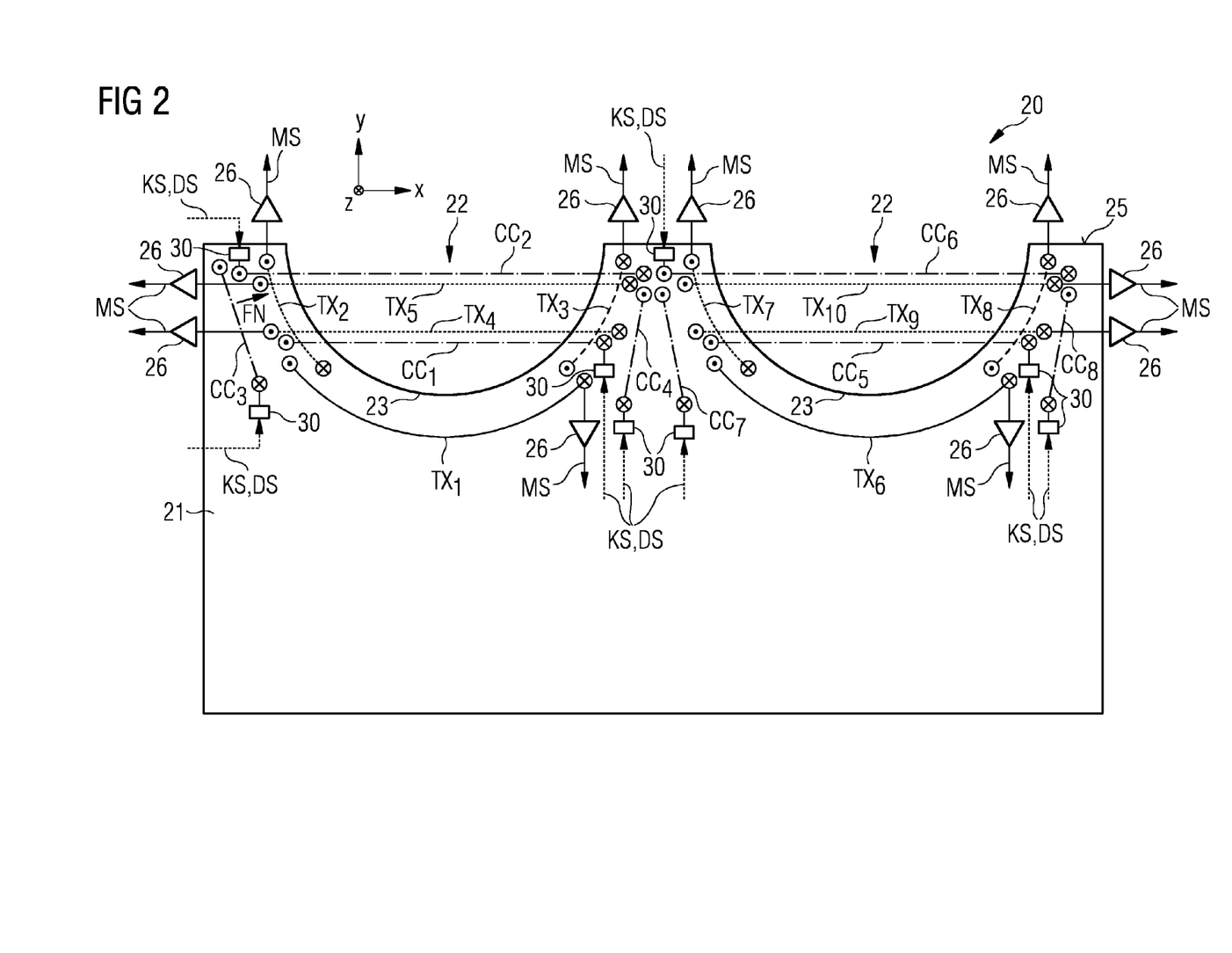
FIG. 2 shows a cross-section through one embodiment of a breast coil.
Figure 3:
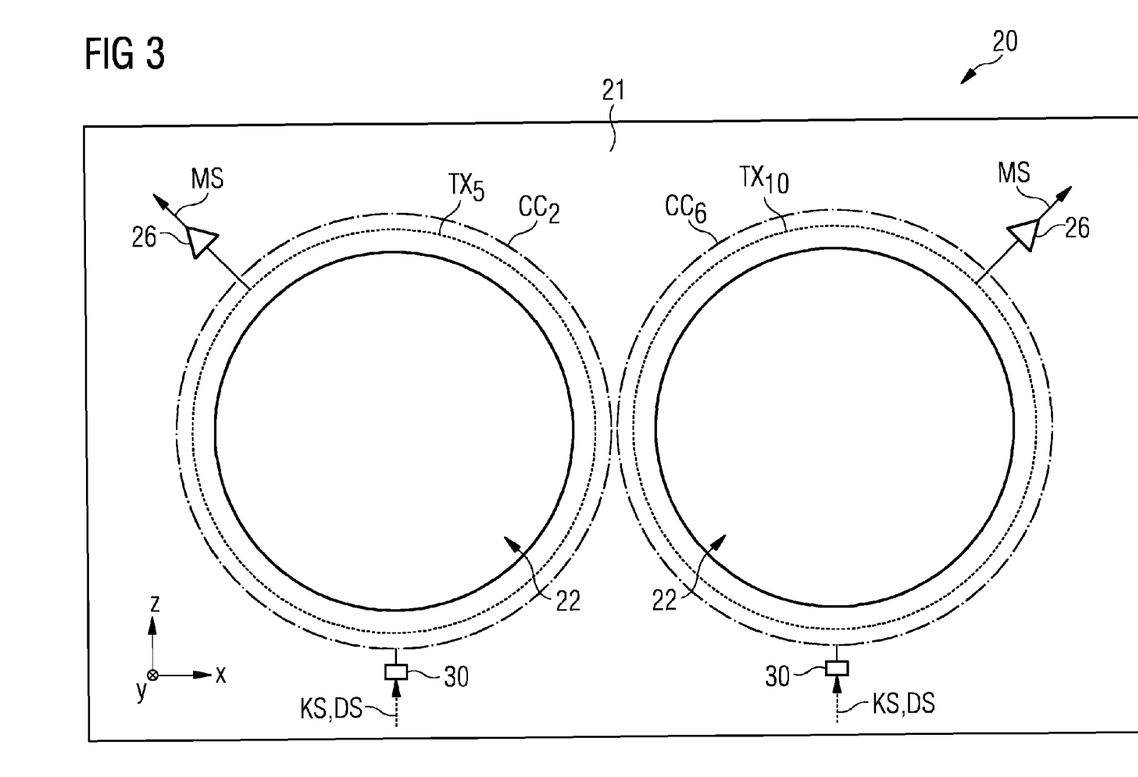
FIG. 3 shows a plan view of one embodiment of the breast coil.

In order to reduce this problem of the asymmetric distribution as far as possible (e.g., to avoid the asymmetric distribution completely), one embodiment of a breast coil includes special HF correction coil elements. This is shown in FIGS. 2 and 3 for a first exemplary embodiment. FIG. 2 shows a schematic cross-section through the breast coil 20, and FIG. 3 shows a plan view of the breast coil 20. The spatial directions conform to the same notation as FIG. 1.

The breast coil 20 includes a housing 21. In the upper side shown in FIG. 2, which shows a chest support area 25 for the patient's body, there are two breast recesses 22 beside each other to accommodate the patient's breasts. The breast recesses 22 may be open on lower sides. In the exemplary embodiment shown, the breast recesses 22 are closed off on the lower side (e.g., on the side opposite to the chest support area 25) by a hemispherical housing wall 23.

The breast coil shown in FIG. 2 includes a plurality of individual receiving coil elements $TX_1, TX_2, TX_3, \ldots, TX_{10}$. Each of the receiving coil elements $TX_1, TX_2, TX_3, \ldots, TX_{10}$ includes a conducting loop, in which a magnetic resonance signal from the breast induces a voltage or current that is then tapped off and amplified in a preamplifier 26. The magnetic resonance signal MS thereby produced is then communicated by a cable or wirelessly to a receiving device in the magnetic resonance tomography device. In the receiving device, further processing of the magnetic resonance signals may then take place, as is explained later.

Some of the receiving coil elements $TX_4, TX_5, TX_9, TX_{10}$ run circularly, each around one breast recess 23 of the breast coil 20. Each of the receiving coil elements $TX_4, TX_5, TX_9, TX_{10}$ receives mainly a signal polarized in the y direction. For each of the breast recesses 22, the plan view in FIG. 3 shows one of the receiving coil elements $TX_5, TX_{10}$ that runs circularly around the breast recess 22.

Underneath the breast recesses 22 and in the housing, there are two receiving coil elements $TX_1$, $TX_6$ that also receive a signal that is mainly polarized in the y direction.

On the right and the left beside each breast recess 22, receiving coil elements $TX_2$, $TX_3$, $TX_7$, $TX_8$ are provided. Each of the receiving coil elements $TX_2$, $TX_3$, $TX_7$, $TX_8$ has conducting loops, for which the antenna area enclosed by the conducting loop is transverse to or perpendicular to the x direction. The receiving coil elements $TX_2$, $TX_3$, $TX_7$, $TX_8$ detect a magnetic resonance signal that is polarized mainly in the x direction.

As well as the receiving coil elements $TX_1$, $TX_2$, $TX_3$, ..., $TX_{10}$, the breast coil 20 also has HF correction coil elements $CC_1$, $CC_2$, ..., $CC_8$. Each of the HF correction coil elements $CC_1$, $CC_2$, ..., $CC_8$ is formed by a conducting loop that is connected to a circuit arrangement 30 (in each of FIGS. 2 and 3 shown only as a single block) such that the HF correction coil element $CC_1$, $CC_2$, ..., $CC_8$ may be switched into an HF correction mode of operation. In the HF correction mode of operation, when a transmission antenna arrangement of the magnetic resonance tomography device emits a $B_1$ field (e.g., using the body coil), the HF correction coil element $CC_1$, $CC_2$, ..., $CC_8$ receives the $B_1$ field and resonates constructively or destructively. The way in which and how strongly the HF correction coil element $CC_1$, $CC_2$, ..., $CC_8$ resonates depends on the precise circuit state (e.g., on the self-resonant frequency, to which the HF correction coil element $CC_1$, $CC_2$, ..., $CC_8$ is tuned). If the self-resonant frequency lies above the magnetic resonance frequency that is being used, then the HF correction coil element $CC_1$, $CC_2$, ..., $CC_8$ resonates constructively. If the self-resonant frequency lies below the magnetic resonance frequency, then the HF correction coil element $CC_1$, $CC_2$, ..., $CC_8$ resonates destructively and thereby reduces the $B_1$ field locally in the region that is "illuminated".

Figure 4:
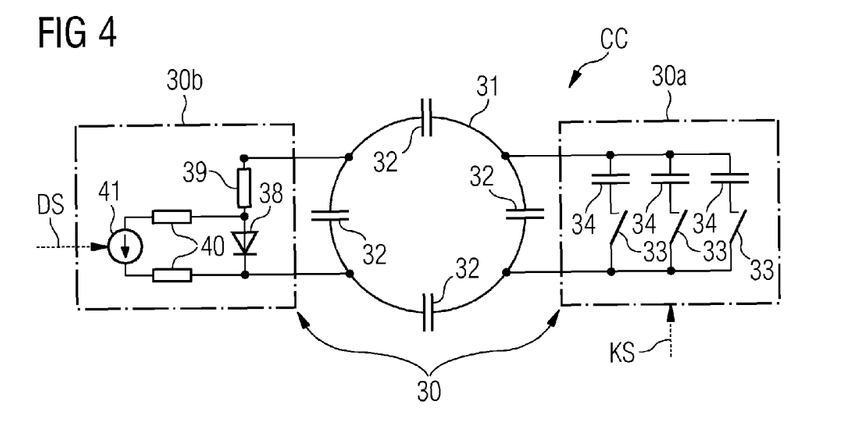
FIG. 4 shows a simplified circuit diagram of a pure HF correction coil element with a circuit arrangement in accordance with a first exemplary embodiment.

A circuit diagram for an exemplary embodiment of a suitable HF correction coil element CC that may be used in the exemplary embodiment of the breast coil 20 shown in FIGS. 2 and 3 is shown in FIG. 4. The HF correction coil element CC includes a conducting loop 31 that is interrupted in several places by capacitive elements 32 (e.g., common capacitors that are also used in magnetic resonance receiving coils). In addition, the HF correction coil element incorporates a circuit arrangement 30 including two sub-circuit arrangements 30a, 30b.

One sub-circuit arrangement 30b includes a switching circuit, in which an inductive element 39 and a switchable diode 38 are connected in parallel across one of the capacitors 32 of the conducting loop 31. This switchable diode 38 is connected through two chokes 40 to a voltage source 41 that may be switched on and off by a deactivation signal DS. If the deactivation signal DS is set, then the sub-circuit arrangement 30b detunes the resonant frequency of the conducting loop 31 so far that the resonant frequency lies far outside the magnetic resonance frequency that is being used, and hence deactivates the entire HF correction coil element CC (e.g., the resonant frequency is invisible in the region of the magnetic resonance frequency).

The other sub-circuit arrangement 30a is used, when not in the deactivated state, to detune the self-resonant frequency of the HF correction coil element CC by connecting further capacitive elements 34 in parallel with a capacitive element 32 of the conducting loop. The self-resonant frequency is detuned such that the self-resonant frequency lies either above or below the magnetic resonance frequency used, but in a range such that the HF correction coil element CC still resonates constructively or destructively in the $B_1$ field. Consequently, the self-resonant frequency manipulates the $B_1$ field locally. For this purpose, each of the individual capacitive elements 34 of the sub-circuit arrangement 30a may be switched in separately with switches 33 that may be actuated by a correction signal KS. The switches 33 may be in the form, for example, of PIN diode switches or transistors (e.g., BUZ71). The exemplary embodiment shown in FIG. 4 illustrates only an example with three capacitors that may be switched in. However, numerous further switching stages may be used.

Both the correction control signal KS and also the deactivation signal DS may be generated by a suitable correction signal generation device of the magnetic resonance tomography device and communicated to the relevant HF correction coil element CC, as is explained below.

Figure 5:
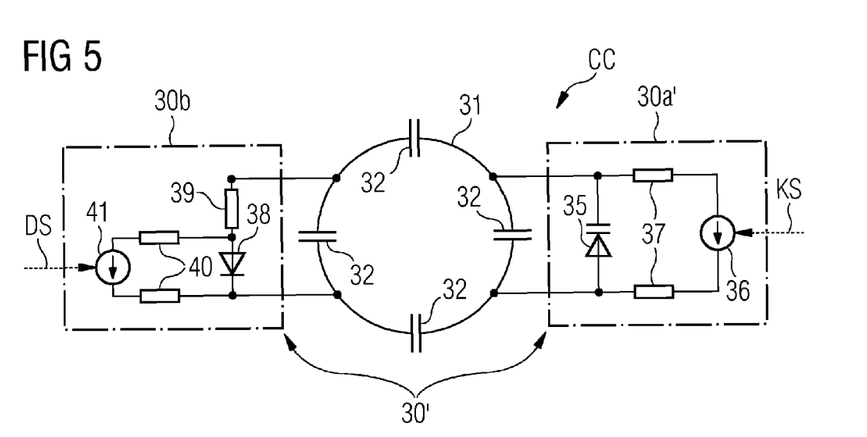
FIG. 5 shows a simplified circuit diagram of a pure HF correction coil element with a circuit arrangement in accordance with a second exemplary embodiment.

FIG. 5 shows a variant of an HF correction coil element with an altered circuit arrangement 30'. The circuit arrangement 30' differs from the circuit arrangement 30 of the exemplary embodiment shown in FIG. 4 only in the sub-circuit arrangement 30a' for tuning the self-resonant frequency of the HF correction coil element CC in the HF correction mode of operation (e.g., when the HF correction coil element CC is not deactivated). The sub-circuit arrangement 30a' is configured such that instead of several discrete capacitive elements 34, as in the exemplary embodiment shown in FIG. 4, one variable capacitance diode 35 may be steplessly adjusted via an adjustable voltage source 36 that is connected to the variable capacitance diode 35 through chokes 37 using a correction signal KS. Using variable capacitance diode 35, the self-resonant frequency may be fine tuned within a particular range, so that the effect of the HF correction element CC may be adjusted even more accurately than in the exemplary embodiment shown in FIG. 4. Consequently, an even better homogenization is possible. The exemplary embodiment shown in FIG. 4 has the advantage that relatively simple capacitive elements 34, with an adequately high voltage endurance of more than 100 V, may be cost-effectively used.

As shown in FIG. 2 and in FIG. 3, there are pairs of HF correction coil elements $CC_1$, $CC_2$, and $CC_5$, $CC_6$. Each pair is arranged on a different plane parallel to the chest support area 25 of the breast coil 20, and each of the pair is arranged circularly around one breast recess 22. The HF correction coil elements $CC_1$, $CC_2$, $CC_5$, $CC_6$ manipulate primarily a portion, polarized in the y direction, of the $B_1$ field that is generally circularly polarized.

In addition, there are, arranged by the side of each breast recess 22, further HF correction coil elements $CC_3$, $CC_4$, $CC_7$, $CC_8$. These HF correction coil elements $CC_3$, $CC_4$, $CC_7$, $CC_8$ are in the form of conducting loops and circumscribe an effective antenna area that is arranged transverse to the x direction. A vector normal FN to this antenna area is shown for the HF correction coil element on the far left in FIG. 2. As shown, the normal vector FN is, to within a small angle, parallel to the x direction (e.g., to an imaginary connecting line between the two breast recesses 22 of the breast coil 20). Using the HF correction coil elements $CC_3$, $CC_4$, $CC_7$, $CC_8$, a portion of the $B_1$ field polarized primarily in the x direction is then manipulated.

Overall, using the arrangement of the HF correction coil elements shown in FIG. 2, the $B_1$ field may be manipulated relatively well and in a simple way so that the entire breast region is substantially more uniformly illuminated (e.g., the $B_1$ field is more homogenized than without these HF correction coil elements $CC_1$, $CC_2$, $CC_3$, $CC_4$, $CC_5$, $CC_6$, $CC_7$, $CC_8$).

Figure 6:
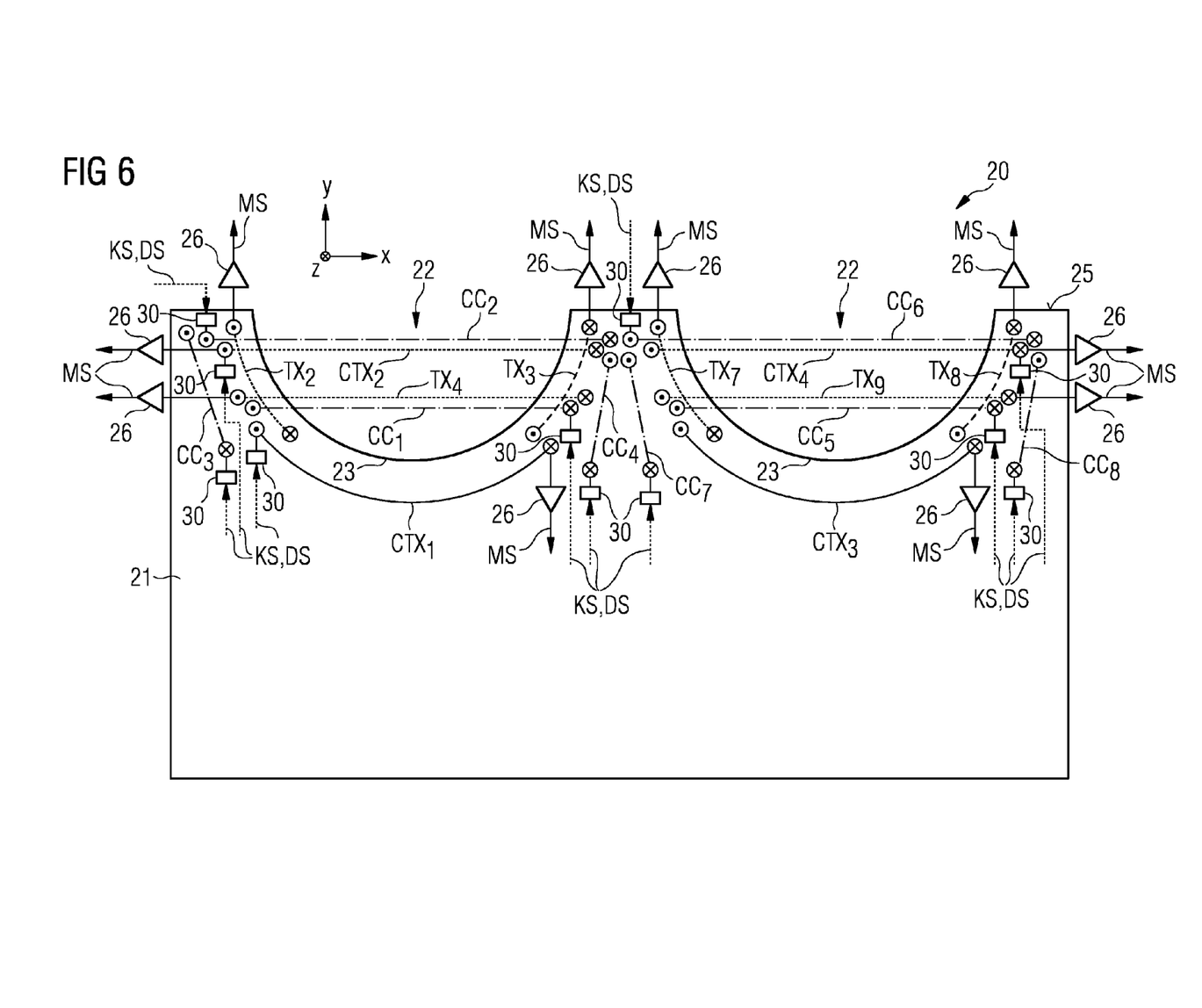
FIG. 6 shows a cross-section through one embodiment of a breast coil.

FIG. 6 shows another exemplary embodiment of a breast coil 20. This exemplary embodiment is very similar to the exemplary embodiment shown in FIGS. 2 and 3. However, some of the receiving coil elements are configured such that the receiving coil elements may also be used simultaneously as HF correction coil elements during the transmission mode of operation. Some of the antenna elements are constructed as combined receiving/correction coil elements $CTX_1$, $CTX_2$, $CTX_3$, $CTX_4$. This is shown symbolically in FIG. 6 in that each of the combined receiving/correction coil elements $CTX_1$, $CTX_2$, $CTX_3$, $CTX_4$ is connected not only to a preamplifier 26 in order to be able to output a magnetic resonance signal MS, but is also provided with a circuit arrangement 30.

Figure 7:
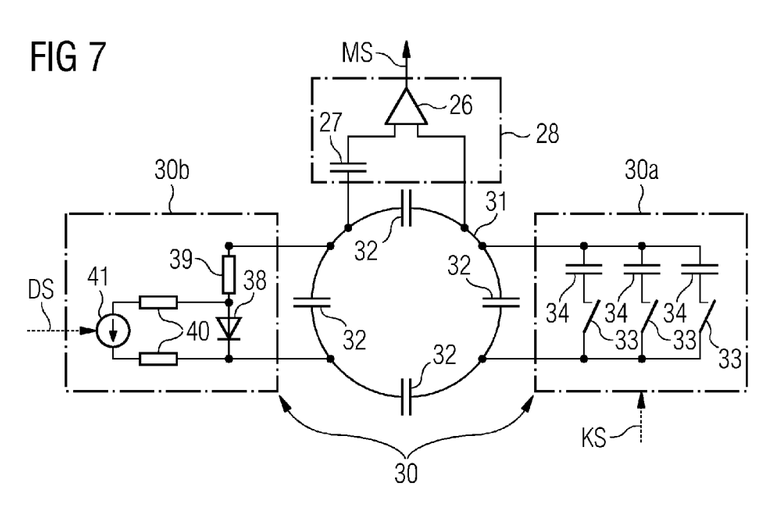
FIG. 7 shows a simplified circuit diagram of an HF correction coil element with a receiving function, with a circuit arrangement in accordance with a first exemplary embodiment.
Figure 8:
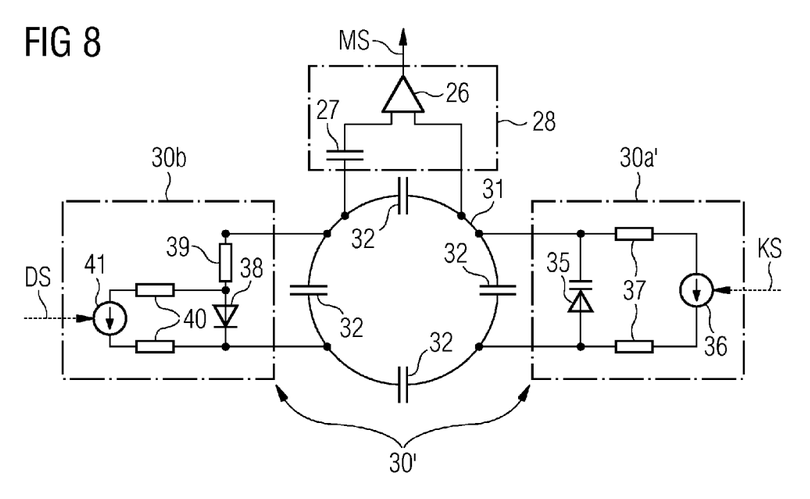
FIG. 8 shows a simplified circuit diagram of an HF correction coil element with a receiving function, with a circuit arrangement in accordance with a second exemplary embodiment.

Circuit diagrams for such receiving/correction coil elements CTX are shown in FIGS. 7 and 8. The circuit arrangements 30, 30' for the use of the receiving/correction coil elements CTX as HF correction coil elements are constructed correspondingly to the circuit arrangements 30, 30' in the exemplary embodiment shown in FIGS. 4 and 5. When the receiving/correction coil elements CTX are not in the deactivated state, a self-resonant frequency that corresponds as exactly as possible with the magnetic resonance frequency that is being used is set. This is then the receiving mode of operation. In addition, each of the receiving/correction coil elements CTX is also equipped with a receiving circuit arrangement 28, with which the magnetic resonance signal that is received is tapped off across one of the capacitive elements 32 in the conducting loop 31 using a preamplifier 26 that, on one side, is connected via a capacitive element 27 to the conducting loop 31.

FIG. 7 shows again, analogous to FIG. 4, an exemplary embodiment with discrete different circuit states (e.g., precisely predefined discrete self-resonant frequencies for various HF correction modes of operation or for setting the receiving state of operation). FIG. 8 shows, analogous to the exemplary embodiment shown in FIG. 5, a sub-circuit arrangement 30a, with which the self-resonant frequency of the coil element CTX may be steplessly detuned over a particular range, where the receiving mode of operation lies within the range of self-resonant frequencies that may be reached by the sub-circuit arrangement 30a.

All the HF receiving coil elements may be equipped as HF correction coil elements in order to save on the total of coil elements. A functional separation of the receiving coil elements and the HF correction coil elements has the following advantages. The HF receiving coil elements may be configured and adapted independently of the requirements to be met by the resonating HF correction coil elements. For the HF receiving coil elements, more cost-effective and smaller components (e.g., capacitors, diodes, and coils) with lower losses may be used, because the HF receiving coil elements do not absolutely need to have the same power withstand capacity as in the case of the resonating HF correction coil elements.

The resonating HF correction coil elements may be constructed such that field structures of the resonating HF correction coil elements optimally compensate the $B_1$ distortions. This configuration is then independent of the HF receiving coil elements, which will instead be developed from the point of view of an optimal signal/noise ratio and of being used for parallel imaging (e.g., close to the patient, many elements in typical phase encoding directions).

The receiving coil elements may additionally be deployed as transmission coil elements, and the receiving coil elements may be provided with a circuit arrangement that permits active emission of a $B_1$ field.

Figure 9:
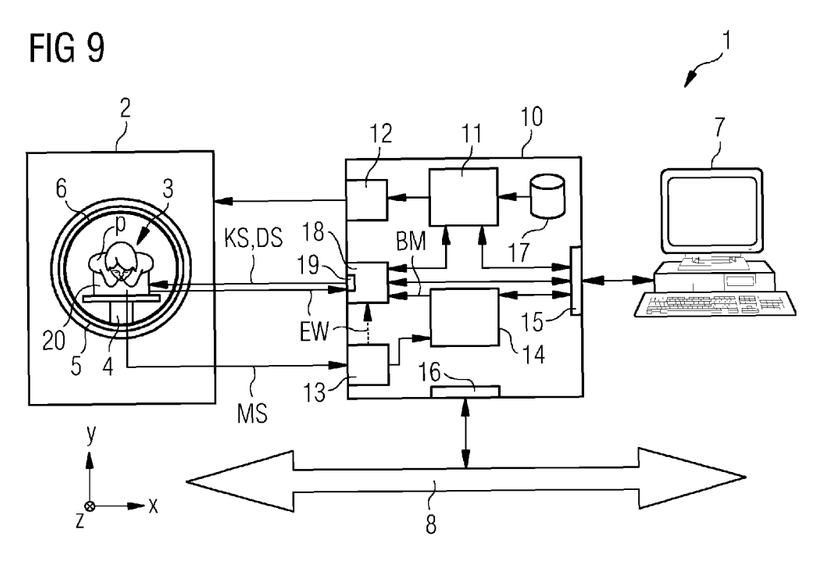
FIG. 9 shows a diagram of an exemplary embodiment of a magnetic resonance tomography device.

FIG. 9 shows a schematic diagram of one embodiment of a magnetic resonance tomography device 1 (also referred to below as an MR system), in which a breast coil 20 may be used.

The heart of the magnetic resonance tomography device 1 is a normal commercial tomograph 2 (e.g., a scanner 2), in which a female patient is positioned on a patient table 4 within a cylindrical measurement space 3 (e.g., a patient tunnel). The patient lies on a breast coil 20 so that her breasts are accommodated in the breast recesses 22. The patient tunnel 3 is surrounded by an HF transmission antenna arrangement 6 for emitting the $B_1$ field (e.g., a birdcage antenna). The $B_1$ field is circularly or elliptically polarized about the z direction, which corresponds to the longitudinal direction of the patient tunnel 3. Outside the HF transmission antenna arrangement 6, there is a magnetic coil system 5 including a basic field magnet and several gradient coils to apply the gradient magnetic field in the desired way.

The scanner 2 and the patient table 4 are actuated by a controller 10 (e.g., a central control device). The controller computer 10 may may be a normal central control computer. The controller 10 is equipped with an appropriate control interface 12 together with a measurement control unit 11. The measurement control unit 11 controls the scanner 2 in accordance with a prescribed measurement protocol to carry out a measurement.

The control interface 12 is shown only as a block. However, this interface 12 includes a plurality of individual interfaces. These include, for example, interfaces for driving the gradient system and/or a high frequency transmission system for emitting the high frequency pulses. The control interface 11 also incorporates an interface for passing control signals over to the patient table 4.

The magnetic resonance signals MS acquired by the scanner 2 (referred to below as the "raw data") are received by the control computer 10 via a receiving interface 13. The receiving interface may also include several sub-interfaces. The raw data MS is then passed over to the reconstruction device 14 that, by a Fourier transformation, reconstructs image data from the raw data MS. The image data is, for example, displayed locally on a screen of a terminal 7 and/or is stored in a store 17 and/or is passed via a network interface 16 to a data bus 8, through which the MR system 1 is linked to other facilities within a network (e.g., in order to store measurement data or reconstructed image data on large mass storage devices or to transmit the measurement data or the reconstructed image data to diagnosis stations).

Actuation of the entire MR system 1 by an operator is effected via the terminal 7, which is linked to the central control unit 10 via a terminal interface 15. With the help of the terminal 7 and a user interface realized on the terminal 7, a user may, for example, select a measurement protocol out of a store 17, if necessary, adapt the measurement protocol, and provide that the measurement control unit 11 outputs to the scanner 2, via the control interface 12, appropriate control signals based on this protocol so that the measurement may be carried out.

The central control device 10 and the scanner 2 may have a plurality of other components, which a magnetic resonance tomography device 1 may have. However, all these components, together with the basic way of functioning of imaging systems of this type, are familiar to the person skilled in the art and therefore do not need to be explained in more detail here.

In one embodiment, the magnetic resonance tomography device 1 also includes a correction signal generation device 18 that is realized on the central control computer 10. This correction signal generation device 18 may accept $B_1$ field distribution data that represents a $B_1$ field distribution and/or the deviation of a current $B_1$ field distribution from a desired target field distribution. On the basis of this, $B_1$ field distribution data generates a correction signal KS. This correction signal KS may, as in the case of a deactivation signal DS, be communicated to the individual HF correction coil elements of the breast coil 20 via a correction control signal interface 19 (e.g., a control cable) in order to switch the HF correction coil elements, as previously explained by reference to FIGS. 4, 5, 7 and 8, into a particular mode of operation or to tune the self-resonant frequency of the coil elements appropriately.

The $B_1$ field distribution data may be, for example, a $B_1$ map BM that the correction signal generation device 18 obtains, for example, from the reconstruction device 14 based on the magnetic resonance signals MS received. For the purpose of producing such a $B_1$ map BM, a special magnetic resonance experiment is to be conducted. The correction signal generation device 18 provides that the measurement control unit 11 is appropriately actuated and, through the control interface 12, provides that the appropriate pulse sequences are output.

Alternatively or additionally, electrical magnitudes EW (e.g., voltage amplitudes and/or phases, or currents) that are induced in the individual HF correction coil elements during the emission of a $B_1$ field by the transmission antenna arrangement 6 may be measured in these coils to provide $B_1$ field distribution data. For this purpose, the cables may, for example, be equipped with appropriate return lines. For example, the tapping off of such additional electrical magnitudes may be effected in the case of exemplary embodiments of the HF correction coil elements that are used as receiving coil elements, as in FIGS. 7 and 8 via preamplifiers 26 that are to be appropriately equipped for switching over in order to feed back the data. If necessary, however, these signals may be tapped off directly via the line for the magnetic resonance signals MS, before the receiving interface or even in the receiving interface (in FIG. 9, this path is shown as a dashed line).

The correction signal generation device 18 is constructed such that the "right" correction control signals KS are determined in an adjustment procedure (e.g., by checking the $B_1$ map or the electrical magnitudes EW as $B_1$ field distribution data). If it is established on this basis that the $B_1$ field is not adequately homogeneous, another new test will be carried out with a different correction circuit state for the HF correction coil elements. This procedure will be repeated until adequate homogenization is achieved. As explained above, this enables the most diverse settings to be tried out simply and gradually, or an intelligent procedure may be used (e.g., an iterative procedure).

During a subsequent useful measurement, when the $B_1$ field is being emitted by the HF transmission antenna arrangement 6, the correction control signals KS that have been determined are output to the HF correction coil elements, so that the correction control signals KS resonate in the desired manner (e.g., constructively or destructively) to provide homogenization. If this is to be followed by the acquisition of the induced magnetic resonance signals from the breast tissue, the individual HF correction coil elements are deactivated with the help of the deactivation signal DS, or in the case of a combined receiving/correction coil element, the relevant coil element is switched to receiving.

The operator may also actuate the correction signal generation device 18 via the terminal 7, for example, in order to start an adjustment procedure and in order possibly to influence individually the driving of the HF correction coil elements.

The central control device 10 may not be constructed, as shown here, as an integral unit, but may also be in the form of many separate units that are networked with each other in an appropriate way. Many of the components may also be realized in the form of software on suitable microcontrollers. This applies, for example, for the measurement control unit 11, the correction signal generation device 19 and the reconstruction unit 14, or the sub-modules. The components may be realized jointly with other components on one or more computing units (e.g., microcontrollers) that belong to the controller 10.

The breast coils illustrated above, the magnetic resonance tomography device 1 and the method that has been described in detail are only exemplary embodiments that a person skilled in the art could modify in a wide variety of ways without going outside the scope of the invention. For example, the MR system may also be constructed differently than in the exemplary embodiments (e.g., with a measurement space that is open on the side(s)). The use of the indefinite article "a" does not exclude the possibility that multiple instances of the features concerned are present. Apart from this, "units," "modules" and "facilities" may include one or more components that may also be spatially separated.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A breast coil for a magnetic resonance tomography device for producing magnetic resonance recordings of female breasts, the breast coil comprising:
   a coil housing comprising a breast recess to accommodate a breast;
   a plurality of coil elements, wherein at least one coil element of the plurality of coil elements forms a high frequency (HF) correction coil element; and
   a circuit arrangement operable to switch the HF correction coil element between an HF correction mode of operation and another mode of operation,
   wherein the HF correction coil element is configured such that in the HF correction mode of operation, the HF correction coil element resonates passively with a $B_1$ field emitted by a transmission antenna arrangement of the magnetic resonance tomography device, and influences a local $B_1$ field distribution during a magnetic resonance recording.

2. The breast coil as claimed in claim 1, wherein the HF correction coil element is switchable into a receiving mode of operation in order to receive a magnetic resonance signal and pass the magnetic resonance signal to a processing unit.

3. The breast coil as claimed in claim 1, further comprising:
   a coil element arrangement that incorporates a plurality of receiving coil elements operable to receive a magnetic resonance signal and pass the magnetic resonance signal to a processing unit; and
   a plurality of separate HF correction coil elements that cannot be switched over into a receiving mode of operation.

4. The breast coil as claimed in claim 1, wherein the circuit arrangement of the HF correction coil element is configured such that the HF correction coil element is switchable over between several discrete HF correction modes of operation.

5. The breast coil as claimed in claim 1, wherein the circuit arrangement of the HF correction coil element is configured such that the HF correction coil element is switchable steplessly between different HF correction modes of operation.

6. The breast coil as claimed in claim 1, wherein the HF correction coil element is configured and arranged such that the HF correction coil element detects a $B_1$ field that is polarized in a direction that runs essentially perpendicularly to a plane of an opening in the breast recess.

7. The breast coil as claimed in claim 6, wherein the HF correction coil element comprises a conducting loop that runs essentially circularly around an opening in the breast recess.

8. The breast coil as claimed in claim 1, wherein the HF correction coil element is configured and arranged such that the HF correction coil element detects a $B_1$ field that is polarized in a direction that runs essentially parallel to a plane of an opening in the breast recess and perpendicular to a longitudinal axis of the body of a patient.

9. The breast coil as claimed in claim 8, wherein the HF correction coil element comprises a conducting loop that runs essentially on a side beside the breast recess such that a normal to a plane of an antenna area surrounded by the conducting loop lies in a direction that runs essentially parallel to a plane of an opening of the breast recess and perpendicular to a longitudinal axis of the body of a patient.

10. The breast coil as claimed in claim 1, wherein the HF correction coil element comprises an interface for the measurement of an electrical magnitude that is present at the HF correction coil element during an HF correction mode of operation.

11. The breast coil as claimed in claim 2, further comprising:
a coil element arrangement that incorporates a plurality of receiving coil elements operable to receive a magnetic resonance signal and pass the magnetic resonance signal to a processing unit; and
a plurality of separate HF correction coil elements that cannot be switched over into a receiving mode of operation.

12. The breast coil as claimed in claim 2, wherein the circuit arrangement of the HF correction coil element is configured such that the HF correction coil element is switchable over between several discrete HF correction modes of operation.

13. The breast coil as claimed in claim 2, wherein the circuit arrangement of the HF correction coil element is configured such that the HF correction coil element is switchable steplessly between different HF correction modes of operation.

14. The breast coil as claimed in claim 2, wherein the HF correction coil element is configured and arranged such that the HF correction coil element detects a $B_1$ field that is polarized in a direction that runs essentially perpendicularly to a plane of an opening in the breast recess.

15. The breast coil as claimed in claim 14, wherein the HF correction coil element comprises a conducting loop that runs essentially circularly around an opening in the breast recess.

16. A magnetic resonance tomography device for producing magnetic resonance recordings of a female breast, the magnetic resonance tomography device comprising:
a breast coil comprising:
a coil housing comprising a breast recess to accommodate a breast;
a plurality of coil elements, wherein at least one coil element of the plurality of coil elements forms a high frequency (HF) correction coil element; and
a circuit arrangement operable to switch the HF correction coil element between an HF correction mode of operation and another mode of operation,
wherein the HF correction coil element is configured such that in the HF correction mode of operation, the HF correction coil element resonates passively with a $B_1$ field emitted by a transmission antenna arrangement of the magnetic resonance tomography device, and influences a local $B_1$ field distribution during a magnetic resonance recording.

17. The magnetic resonance tomography device as claimed in claim 16, further comprising:
a correction signal generation device configured to generate a correction control signal for the HF correction coil element on the basis of $B_1$ field distribution data that represents a $B_1$ field distribution, a deviation of a current $B_1$ field distribution from a target $B_1$ field distribution, or the $B_1$ field distribution and the deviation of the current $B_1$ field distribution from the target $B_1$ field distribution; and
a correction control signal interface operable to output the correction control signal to the HF correction coil element.

18. A method for producing magnetic resonance recordings of a breast in a magnetic resonance tomography device, the magnetic resonance tomography device comprising a transmission antenna arrangement and a breast coil, the breast coil comprising a coil housing having a breast recess to accommodate a breast, and a plurality of coil elements, the method comprising:
emitting a $B_1$ field with the transmission antenna arrangement; and
receiving, by a coil element of the plurality of coil elements, magnetic resonance signals excited in the breast as a result of the $B_1$ field,
wherein when the $B_1$ field is being emitted, the coil element of another coil element of the plurality of coil elements is switched into an HF correction mode of operation, so that the coil element or the other coil element resonates passively with the $B_1$ field and influences a local $B_1$ field distribution.

19. The method as claimed in claim 18, further comprising:
detecting $B_1$ field distribution data that represents a $B_1$ field distribution, a deviation of a current $B_1$ field distribution from a target $B_1$ field distribution, or the $B_1$ field distribution and the deviation of the current $B_1$ field distribution from the target $B_1$ field distribution, in an adjustment operation;
actuating the HF correction coil element based on the detected $B_1$ field distribution data during a useful magnetic resonance measurement.

20. The method as claimed in claim 19, wherein the actuation of the HF correction coil element is varied during the useful magnetic resonance measurement.

\* \* \* \* \*